United States Patent
Helf et al.

(10) Patent No.: US 9,061,821 B2
(45) Date of Patent: **\*Jun. 23, 2015**

(54) APPARATUS FOR CONTROL OF A VOLATILE MATERIAL DISPENSER

(71) Applicant: S.C. Johnson & Son, Inc., Racine, WI (US)

(72) Inventors: Thomas A. Helf, New Berlin, WI (US); Edward L. Paas, Los Altos, CA (US); Paul E. Furner, Racine, WI (US); Rene Maurice Beland, Waterford, WI (US); James F. Kimball, Greenfield, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/024,355

(22) Filed: Sep. 11, 2013

(65) Prior Publication Data
US 2014/0008385 A1 Jan. 9, 2014

Related U.S. Application Data

(63) Continuation of application No. 11/893,489, filed on Aug. 16, 2007, now Pat. No. 8,556,122.

(51) Int. Cl.
| | |
|---|---|
| *B67D 1/00* | (2006.01) |
| *B65D 83/46* | (2006.01) |
| *A61L 9/14* | (2006.01) |
| *B65D 83/26* | (2006.01) |
| *B65D 83/38* | (2006.01) |
| *G04C 23/48* | (2006.01) |

(Continued)

(52) U.S. Cl.
CPC . *B65D 83/46* (2013.01); *A61L 9/14* (2013.01); *A61L 2209/111* (2013.01); *B05B 12/004* (2013.01); *B05B 12/12* (2013.01); *B65D 83/20* (2013.01); *B65D 83/262* (2013.01); *B65D 83/386* (2013.01); *G04C 23/48* (2013.01)

(58) Field of Classification Search
CPC .............................. B65D 83/386; B65D 83/46
USPC ............... 222/52, 61, 63, 162, 164, 654–649, 222/504, 402.21; 239/70, 332

See application file for complete search history.

(56) References Cited

U.S. PATENT DOCUMENTS

| | | | |
|---|---|---|---|
| 2,608,319 | A | 8/1952 | Petry |
| 2,613,108 | A | 10/1952 | Kraus |

(Continued)

FOREIGN PATENT DOCUMENTS

| | | |
|---|---|---|
| EP | 656230 | 6/1995 |
| EP | 0826607 | 3/1998 |

(Continued)

OTHER PUBLICATIONS

JP 61-232177. Partial English Translation. pp. 1-2.

(Continued)

*Primary Examiner* — Daniel R Shearer

(57) ABSTRACT

A volatile material dispenser includes a housing adapted to receive a container that includes a tilt-activated valve stem. The housing includes a resilient retaining structure. The resilient retaining structure is adapted to retain a portion of the container. An electric drive unit is disposed within the housing. The drive unit includes a cam for engaging a portion of the container to actuate the valve stem.

17 Claims, 15 Drawing Sheets

(51) Int. Cl.
  *B05B 12/00* (2006.01)
  *B05B 12/12* (2006.01)
  *B65D 83/20* (2006.01)

(56) References Cited

U.S. PATENT DOCUMENTS

| | | | |
|---|---|---|---|
| 2,928,573 A | 3/1960 | Edelstein | |
| 3,018,056 A | 1/1962 | Montgomery | |
| 3,115,277 A | 12/1963 | Montague, Jr. | |
| 3,127,060 A | 3/1964 | Vosbikian et al. | |
| 3,139,218 A | 6/1964 | Cairelli | |
| 3,165,238 A | 1/1965 | Wiley | |
| 3,180,532 A | 4/1965 | Michel | |
| 3,185,356 A | 5/1965 | Venus, Jr. | |
| 3,199,732 A | 8/1965 | Strachan | |
| 3,228,609 A * | 1/1966 | Edelstein et al. | 239/70 |
| 3,240,389 A | 3/1966 | Genua | |
| 3,269,602 A | 8/1966 | Webber, III | |
| 3,273,610 A | 9/1966 | Frost | |
| 3,289,886 A | 12/1966 | Goldsholl et al. | |
| 3,305,134 A | 2/1967 | Carmichael et al. | |
| 3,326,418 A | 6/1967 | Kropp | |
| 3,329,314 A | 7/1967 | Kolodziej | |
| 3,368,717 A | 2/1968 | Weber, III | |
| 3,398,864 A | 8/1968 | Kolodziej | |
| 3,411,670 A | 11/1968 | Mangel | |
| 3,419,189 A | 12/1968 | Iketani | |
| 3,455,485 A | 7/1969 | Crownover | |
| 3,477,613 A | 11/1969 | Mangel | |
| 3,497,108 A | 2/1970 | Mason | |
| 3,497,110 A | 2/1970 | Bombero et al. | |
| 3,518,464 A | 6/1970 | Hitoshi et al. | |
| 3,542,248 A | 11/1970 | Mangel | |
| 3,543,122 A | 11/1970 | Klebanoff et al. | |
| 3,584,766 A | 6/1971 | Hart et al. | |
| 3,589,562 A | 6/1971 | Buck | |
| 3,589,563 A | 6/1971 | Carragan et al. | |
| 3,591,058 A | 7/1971 | Johnston | |
| 3,617,214 A | 11/1971 | Dolac | |
| 3,620,023 A | 11/1971 | Schmid | |
| 3,627,176 A | 12/1971 | Sailors | |
| 3,632,020 A | 1/1972 | Nixon, Jr. et al. | |
| 3,643,836 A | 2/1972 | Hunt | |
| 3,658,209 A | 4/1972 | Freeman et al. | |
| 3,664,548 A | 5/1972 | Broderick | |
| 3,666,144 A | 5/1972 | Winder | |
| 3,671,825 A | 6/1972 | Allison | |
| 3,677,441 A | 7/1972 | Nixon, Jr. et al. | |
| 3,690,519 A | 9/1972 | Wassilieff | |
| 3,722,749 A | 3/1973 | Ishida | |
| 3,726,437 A | 4/1973 | Siegel | |
| 3,732,509 A | 5/1973 | Florant et al. | |
| 3,739,944 A | 6/1973 | Rogerson | |
| 3,756,465 A | 9/1973 | Meshberg | |
| 3,794,216 A | 2/1974 | Buck | |
| 3,817,429 A | 6/1974 | Smrt | |
| 3,841,525 A | 10/1974 | Siegel | |
| 3,870,274 A | 3/1975 | Broe | |
| 3,871,557 A * | 3/1975 | Smrt | 222/162 |
| 3,885,712 A | 5/1975 | Libit | |
| 3,929,259 A | 12/1975 | Fegley et al. | |
| 3,952,916 A | 4/1976 | Phillips | |
| 3,968,905 A | 7/1976 | Pelton | |
| 3,974,941 A | 8/1976 | Mettler | |
| 3,980,205 A | 9/1976 | Smart | |
| 4,004,550 A | 1/1977 | White et al. | |
| 4,006,844 A | 2/1977 | Corris | |
| 4,063,664 A | 12/1977 | Meetze, Jr. | |
| 4,064,573 A | 12/1977 | Calderone | |
| 4,068,575 A | 1/1978 | Difley et al. | |
| 4,068,780 A | 1/1978 | Fegley | |
| 4,077,542 A | 3/1978 | Petterson | |
| 4,096,974 A | 6/1978 | Haber et al. | |
| 4,184,612 A | 1/1980 | Freyre | |
| 4,235,373 A | 11/1980 | Clark | |
| 4,238,055 A | 12/1980 | Staar | |
| 4,275,821 A | 6/1981 | Lanno et al. | |
| 4,396,152 A | 8/1983 | Abplanalp | |
| 4,415,797 A | 11/1983 | Choustoulakis | |
| 4,483,466 A | 11/1984 | Gutierrez | |
| 4,544,086 A | 10/1985 | Hill et al. | |
| 4,625,342 A * | 12/1986 | Gangnath et al. | 4/228.1 |
| 4,658,985 A | 4/1987 | Madsen et al. | |
| 4,671,431 A * | 6/1987 | Obrist | 222/327 |
| 4,702,418 A | 10/1987 | Carter et al. | |
| 4,877,989 A | 10/1989 | Drews et al. | |
| 4,967,935 A | 11/1990 | Celest | |
| 4,989,755 A | 2/1991 | Shiau | |
| 4,993,570 A | 2/1991 | Julian et al. | |
| 5,012,961 A | 5/1991 | Madsen et al. | |
| 5,014,881 A | 5/1991 | Andris | |
| 5,018,963 A | 5/1991 | Diederich | |
| 5,025,962 A | 6/1991 | Renfo | |
| 5,029,729 A | 7/1991 | Madsen et al. | |
| 5,038,972 A | 8/1991 | Muderlak et al. | |
| 5,055,822 A | 10/1991 | Campbell et al. | |
| 5,098,291 A | 3/1992 | Curtis et al. | |
| 5,134,961 A | 8/1992 | Giles et al. | |
| 5,154,323 A | 10/1992 | Query et al. | |
| 5,198,157 A | 3/1993 | Bechet | |
| 5,221,025 A * | 6/1993 | Privas | 222/1 |
| 5,249,718 A | 10/1993 | Muderlak | |
| 5,297,988 A | 3/1994 | Nishino et al. | |
| 5,337,926 A | 8/1994 | Drobish et al. | |
| 5,337,929 A | 8/1994 | Van der Heijden | |
| 5,342,584 A | 8/1994 | Fritz et al. | |
| 5,353,744 A | 10/1994 | Custer | |
| 5,364,028 A | 11/1994 | Wozniak | |
| 5,383,580 A | 1/1995 | Winder | |
| RE34,847 E | 2/1995 | Muderlak et al. | |
| 5,392,768 A | 2/1995 | Johansson et al. | |
| 5,397,028 A | 3/1995 | Jesadanont | |
| 5,445,324 A | 8/1995 | Berry et al. | |
| 5,447,273 A | 9/1995 | Wozniak | |
| 5,447,277 A | 9/1995 | Schlüter et al. | |
| 5,449,117 A | 9/1995 | Muderlak et al. | |
| 5,489,047 A | 2/1996 | Winder | |
| 5,503,303 A | 4/1996 | LaWare et al. | |
| 5,522,722 A | 6/1996 | Diederich | |
| 5,531,344 A | 7/1996 | Winner | |
| 5,540,359 A | 7/1996 | Gobbel | |
| 5,542,605 A | 8/1996 | Campau | |
| 5,549,228 A | 8/1996 | Brown | |
| 5,588,565 A | 12/1996 | Miller | |
| 5,601,235 A | 2/1997 | Booker et al. | |
| 5,622,162 A | 4/1997 | Johansson et al. | |
| 5,673,825 A | 10/1997 | Chen | |
| 5,676,283 A | 10/1997 | Wang | |
| 5,685,456 A | 11/1997 | Goldstein | |
| 5,695,091 A | 12/1997 | Winings et al. | |
| 5,702,036 A | 12/1997 | Ferrara, Jr. | |
| 5,743,251 A | 4/1998 | Howell et al. | |
| 5,772,074 A | 6/1998 | Dial et al. | |
| 5,787,947 A | 8/1998 | Hertsgaard | |
| 5,791,524 A | 8/1998 | Demarest | |
| 5,810,265 A | 9/1998 | Cornelius et al. | |
| 5,823,390 A | 10/1998 | Muderlak et al. | |
| 5,842,602 A | 12/1998 | Pierpoint | |
| 5,853,129 A | 12/1998 | Spitz | |
| 5,884,808 A | 3/1999 | Muderlak et al. | |
| 5,908,140 A | 6/1999 | Muderlak et al. | |
| 5,922,247 A | 7/1999 | Shoham et al. | |
| 5,924,597 A | 7/1999 | Lynn | |
| 5,938,076 A | 8/1999 | Ganzeboom | |
| 5,964,403 A | 10/1999 | Miller et al. | |
| 6,000,658 A | 12/1999 | McCall, Jr. | |
| 6,006,957 A | 12/1999 | Kunesh | |
| 6,036,108 A | 3/2000 | Chen | |
| 6,039,212 A | 3/2000 | Singh | |
| 6,089,410 A | 7/2000 | Ponton | |
| 6,145,712 A | 11/2000 | Benoist | |
| 6,182,904 B1 | 2/2001 | Ulczynski et al. | |
| 6,216,925 B1 | 4/2001 | Garon | |
| 6,220,293 B1 | 4/2001 | Rashidi | |

(56) References Cited

U.S. PATENT DOCUMENTS

| | | |
|---|---|---|
| 6,237,812 B1 | 5/2001 | Fukada |
| 6,249,717 B1 | 6/2001 | Nicholson et al. |
| 6,254,065 B1 | 7/2001 | Ehrensperger et al. |
| 6,260,739 B1 | 7/2001 | Hsiao |
| 6,267,297 B1 | 7/2001 | Contadini et al. |
| 6,276,574 B1 | 8/2001 | Smrt |
| 6,293,442 B1 | 9/2001 | Mollayan |
| 6,293,474 B1 | 9/2001 | Helf et al. |
| 6,321,742 B1 | 11/2001 | Schmidt et al. |
| 6,338,424 B2 | 1/2002 | Nakamura et al. |
| 6,343,714 B1 | 2/2002 | Tichenor |
| 6,394,310 B1 | 5/2002 | Muderlak et al. |
| 6,409,093 B2 | 6/2002 | Ulczynski et al. |
| 6,419,122 B1 | 7/2002 | Chown |
| 6,454,185 B2 | 9/2002 | Fuchs |
| 6,478,199 B1 | 11/2002 | Shanklin et al. |
| 6,510,561 B1 | 1/2003 | Hammond et al. |
| 6,517,009 B2 | 2/2003 | Yahav |
| 6,533,141 B1 | 3/2003 | Petterson et al. |
| 6,540,155 B1 | 4/2003 | Yahav |
| 6,554,203 B2 | 4/2003 | Hess et al. |
| 6,567,613 B2 | 5/2003 | Rymer |
| 6,588,627 B2 | 7/2003 | Petterson et al. |
| 6,612,464 B2 | 9/2003 | Petterson et al. |
| 6,616,363 B1 | 9/2003 | Guillaume et al. |
| 6,619,562 B2 | 9/2003 | Hamaguchi et al. |
| 6,644,507 B2 | 11/2003 | Borut et al. |
| 6,645,307 B2 | 11/2003 | Fox et al. |
| 6,669,105 B2 | 12/2003 | Bryan et al. |
| 6,688,492 B2 | 2/2004 | Jaworski et al. |
| 6,694,536 B1 | 2/2004 | Haygreen |
| 6,701,663 B1 | 3/2004 | Hughel et al. |
| 6,708,849 B1 | 3/2004 | Carter et al. |
| D488,548 S | 4/2004 | Lablaine |
| 6,722,529 B2 | 4/2004 | Ceppaluni et al. |
| 6,739,479 B2 | 5/2004 | Contadini et al. |
| 6,769,580 B2 | 8/2004 | Muderlak et al. |
| 6,776,968 B2 | 8/2004 | Edwards et al. |
| 6,785,911 B1 | 9/2004 | Percher |
| 6,790,408 B2 | 9/2004 | Whitby et al. |
| 6,832,701 B2 | 12/2004 | Schiller |
| 6,837,396 B2 | 1/2005 | Jaworski et al. |
| 6,843,465 B1 | 1/2005 | Scott |
| 6,877,636 B2 | 4/2005 | Speckhart et al. |
| 6,918,512 B2 | 7/2005 | Kondoh |
| 6,926,002 B2 | 8/2005 | Scarrott et al. |
| 6,926,172 B2 | 8/2005 | Jaworski et al. |
| 6,926,211 B2 | 8/2005 | Bryan et al. |
| 6,938,796 B2 | 9/2005 | Blacker et al. |
| 6,971,560 B1 | 12/2005 | Healy et al. |
| 6,974,091 B2 | 12/2005 | McLisky |
| 6,978,947 B2 | 12/2005 | Jin |
| D513,433 S | 1/2006 | Lemaire |
| 6,997,349 B2 | 2/2006 | Blacker et al. |
| 7,000,853 B2 | 2/2006 | Fugere |
| 7,028,917 B2 | 4/2006 | Buthier |
| 7,032,782 B1 | 4/2006 | Ciavarella et al. |
| D520,623 S | 5/2006 | Lablaine |
| 7,044,337 B1 | 5/2006 | Kou |
| 7,051,455 B2 | 5/2006 | Bedford |
| D525,693 S | 7/2006 | Butler et al. |
| D527,472 S | 8/2006 | Barraclough et al. |
| D532,891 S | 11/2006 | Buthier et al. |
| 7,141,125 B2 | 11/2006 | McKechnie et al. |
| D536,059 S | 1/2007 | King et al. |
| D536,082 S | 1/2007 | Pugh |
| 7,168,631 B2 | 1/2007 | Jones |
| 7,182,227 B2 | 2/2007 | Polie et al. |
| D537,914 S | 3/2007 | King et al. |
| D538,915 S | 3/2007 | Anderson et al. |
| 7,192,610 B2 | 3/2007 | Hughes et al. |
| 7,195,139 B2 | 3/2007 | Jaworski et al. |
| D540,931 S | 4/2007 | Luo |
| 7,223,361 B2 | 5/2007 | Kvietok et al. |
| 7,249,720 B2 | 7/2007 | Mathiez |
| 7,882,990 B1 | 2/2011 | Walters et al. |
| 2002/0020756 A1 | 2/2002 | Yahav |
| 2002/0130146 A1 | 9/2002 | Borut et al. |
| 2003/0089734 A1 | 5/2003 | Eberhardt et al. |
| 2003/0132254 A1 | 7/2003 | Giangreco |
| 2004/0011885 A1 | 1/2004 | McLisky |
| 2004/0028551 A1 | 2/2004 | Kvietok et al. |
| 2004/0033171 A1 | 2/2004 | Kvietok et al. |
| 2004/0035949 A1 | 2/2004 | Elkins et al. |
| 2004/0074935 A1 | 4/2004 | Chon |
| 2004/0155056 A1 | 8/2004 | Yahav |
| 2004/0219863 A1 | 11/2004 | Willacy |
| 2005/0004714 A1 | 1/2005 | Chen |
| 2005/0023287 A1 | 2/2005 | Speckhart et al. |
| 2005/0139624 A1 | 6/2005 | Hooks et al. |
| 2005/0155985 A1 | 7/2005 | Meyer |
| 2005/0201944 A1 | 9/2005 | Kvietok et al. |
| 2005/0224596 A1 | 10/2005 | Panopoulos |
| 2005/0247735 A1 | 11/2005 | Muderlak et al. |
| 2005/0252930 A1 | 11/2005 | Contadini et al. |
| 2005/0279853 A1 | 12/2005 | McLeisch et al. |
| 2006/0011737 A1 | 1/2006 | Amenos et al. |
| 2006/0037532 A1 | 2/2006 | Eidson |
| 2006/0060615 A1 | 3/2006 | McLisky |
| 2006/0076366 A1 | 4/2006 | Furner et al. |
| 2006/0081661 A1 | 4/2006 | Lasserre et al. |
| 2006/0083632 A1 | 4/2006 | Hammond et al. |
| 2006/0118658 A1 | 6/2006 | Corkhill et al. |
| 2006/0124477 A1 | 6/2006 | Cornelius et al. |
| 2006/0140901 A1 | 6/2006 | McKechnie |
| 2006/0151546 A1 | 7/2006 | McLisky |
| 2006/0153733 A1 | 7/2006 | Sassoon |
| 2006/0175341 A1 | 8/2006 | Rodrian |
| 2006/0175357 A1 | 8/2006 | Hammond |
| 2006/0175426 A1 | 8/2006 | Schramm et al. |
| 2006/0191955 A1 | 8/2006 | McLisky |
| 2006/0196576 A1 | 9/2006 | Fleming et al. |
| 2006/0210421 A1 | 9/2006 | Hammond et al. |
| 2006/0219740 A1 | 10/2006 | Bayer |
| 2006/0229232 A1 | 10/2006 | Contadini et al. |
| 2006/0243762 A1 | 11/2006 | Sassoon |
| 2007/0012718 A1 | 1/2007 | Schramm et al. |
| 2007/0062980 A1 | 3/2007 | Bates et al. |
| 2007/0071933 A1 | 3/2007 | Gavelli et al. |
| 2007/0087953 A1 | 4/2007 | McKechnie et al. |
| 2007/0093558 A1 | 4/2007 | Harper et al. |
| 2007/0138326 A1 | 6/2007 | Hu |
| 2007/0158359 A1 | 7/2007 | Rodrian |

FOREIGN PATENT DOCUMENTS

| | | |
|---|---|---|
| EP | 0826608 | 3/1998 |
| EP | 1316514 | 6/2003 |
| EP | 1328757 | 5/2006 |
| EP | 1702512 | 9/2006 |
| EP | 1702513 | 9/2006 |
| EP | 1709980 | 10/2006 |
| FR | 1497250 | 10/1967 |
| FR | 2216810 | 8/1974 |
| GB | 1033025 | 6/1966 |
| GB | 1531308 | 11/1978 |
| JP | 56037070 | 4/1981 |
| JP | 56044061 | 4/1981 |
| JP | 56044062 | 4/1981 |
| JP | 56070865 | 6/1981 |
| JP | 57174173 | 10/1982 |
| JP | 61-232177 | 10/1986 |
| JP | 62109760 | 7/1987 |
| JP | 01-223904 | 9/1989 |
| JP | 03-085169 | 4/1991 |
| JP | 03-085170 | 4/1991 |
| JP | 10216577 | 8/1998 |
| JP | 2001048254 | 2/2001 |
| JP | 2002068344 | 3/2002 |
| JP | 2002113398 | 4/2002 |
| JP | 2003033684 | 2/2003 |
| JP | 2003246380 | 9/2003 |
| JP | 2003311191 | 11/2003 |
| JP | 2004298782 | 10/2004 |

(56) References Cited

FOREIGN PATENT DOCUMENTS

| | | |
|---|---|---|
| JP | 2005081223 | 3/2005 |
| JP | 2005246161 | 9/2005 |
| WO | WO95/29106 | 11/1995 |
| WO | WO00/75046 | 12/2000 |
| WO | WO03/037748 | 5/2003 |
| WO | WO03/037750 | 5/2003 |
| WO | WO03/042068 | 5/2003 |
| WO | WO03/062094 | 7/2003 |
| WO | WO03/062095 | 7/2003 |
| WO | WO03/082709 | 10/2003 |
| WO | WO2005/011560 | 2/2005 |
| WO | WO2005/014060 | 2/2005 |
| WO | WO2005/027630 | 3/2005 |
| WO | WO2005/048718 | 6/2005 |
| WO | WO2005/070474 | 8/2005 |
| WO | WO2005/079583 | 9/2005 |
| WO | WO2005/084721 | 9/2005 |
| WO | WO2006/005962 | 1/2006 |
| WO | WO2006/013321 | 2/2006 |
| WO | WO2006/013322 | 2/2006 |
| WO | WO2006/051267 | 5/2006 |
| WO | WO2006/054103 | 5/2006 |
| WO | WO2006/056762 | 6/2006 |
| WO | WO2006/058433 | 6/2006 |
| WO | WO2006/064187 | 6/2006 |
| WO | WO2006074454 | 7/2006 |
| WO | WO2006/087514 | 8/2006 |
| WO | WO2006/087515 | 8/2006 |
| WO | WO2006/095131 | 9/2006 |
| WO | WO2006/134353 | 12/2006 |
| WO | WO2007/028954 | 3/2007 |
| WO | WO2007/036724 | 4/2007 |
| WO | WO2007/045826 | 4/2007 |
| WO | WO2007/045827 | 4/2007 |
| WO | WO2007/045828 | 4/2007 |
| WO | WO2007/045831 | 4/2007 |
| WO | WO2007/045832 | 4/2007 |
| WO | WO2007/045834 | 4/2007 |
| WO | WO2007/045835 | 4/2007 |
| WO | WO2007/045859 | 4/2007 |

OTHER PUBLICATIONS

International Search Report and Written Opinion PCT/US2008009663 dated Dec. 23, 2008.
Machine Translation of JP 2004-298782, 12 pgs.

* cited by examiner

APPARATUS FOR CONTROL OF A VOLATILE MATERIAL DISPENSER

CROSS REFERENCE TO RELATED APPLICATIONS

The present application is a continuation application of U.S. patent application Ser. No. 11/893,489 filed on Aug. 16, 2007.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure relates generally to discharging a fluid from a spray device, and more particularly, to an apparatus for discharging a fluid from a pressurized aerosol container.

2. Description of the Background of the Invention

Aerosol containers are commonly used to store and dispense volatile materials such as air fresheners, deodorants, insecticides, germicides, decongestants, perfumes, and the like. The volatile material is typically stored under compression in a liquid state within a container. A valve assembly on the container controls release of the volatile material contained therein. The valve assembly generally includes a valve stem, wherein activation or opening of the valve assembly allows the volatile material to flow out of the container through the valve stem. In particular, displacement of the valve stem with respect to the valve assembly activates the valve assembly to release the volatile material from the container. The valve stem may be displaced along a longitudinal axis of the valve assembly, i.e., axially, or the valve stem may be tilted or displaced in a direction transverse to the longitudinal axis of the valve assembly, i.e., radially.

Activation of a valve assembly may be accomplished by an automated system or manually. In manual activation, a user may adjust an activation force applied to the valve stem as required to achieve a desired release. Therefore, consideration of applied force requirements is generally less important to design of manually activated valve assemblies. Conventional automated systems may include motor driven linkages that apply downward pressure to depress the valve stem and open the valve assembly within the container. Typically, these actuator mechanisms are unwieldy and are not readily adaptable to be used in a stand-alone manner and/or a hand-held manner. Further, many of these actuator mechanisms exhibit a great deal of power consumption. Generally, valve assemblies that have tilt-activated valve stems require less force for activation than valves having vertically activated valve stems. Valve assemblies that require smaller activation forces are advantageous because such valves require less power to actuate. Decreased power consumption will allow for longer power source life times. Smaller activation forces also allow for simpler, smaller, and/or less costly automated systems.

Existing automated activation systems for tilt-activated valve assemblies utilize complex and cumbersome motor and gear mechanisms and do not adequately reduce power consumption. A need exists for improved operability and functionality over existing activation systems, e.g., use of improved power supplies and drive units, addition of various actuation options, decreased size, and increased efficiency and reliability.

SUMMARY OF THE INVENTION

According to one embodiment, a volatile material dispenser includes a housing adapted to receive a container that includes a tilt-activated valve stem. The housing includes a resilient retaining structure. The resilient retaining structure is adapted to retain a portion of the container. An electric drive unit is disposed within the housing, wherein the drive unit includes a cam for engaging a portion of the container to actuate the valve stem.

According to another embodiment, a volatile material dispenser includes a housing adapted to retain a container in a suspended operable position. The container includes a tilt-activated valve stem. A drive unit is disposed within the housing and the drive unit includes a cam. The cam imparts transverse motion to a body of the container.

Other aspects and advantages of the present invention will become apparent upon consideration of the following detailed description.

DETAILED DESCRIPTION OF THE DRAWINGS

Figure 1:
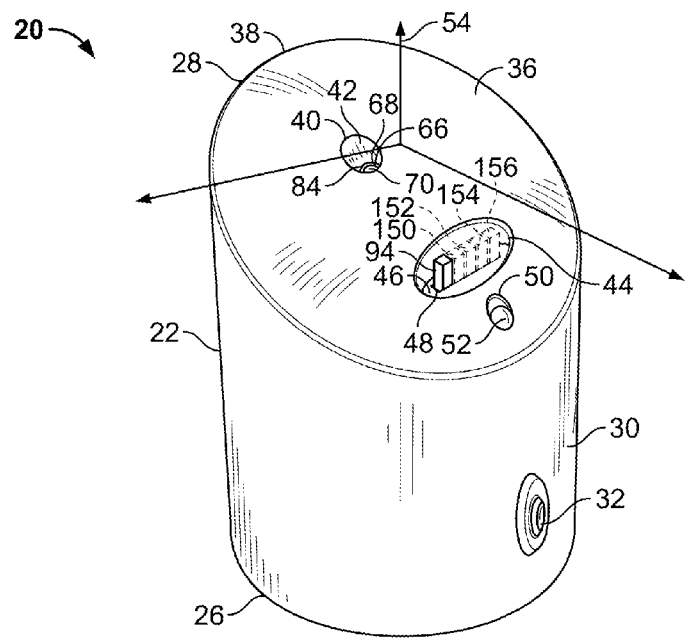
FIG. 1 is an isometric view of one embodiment of an actuator device.
Figure 2:
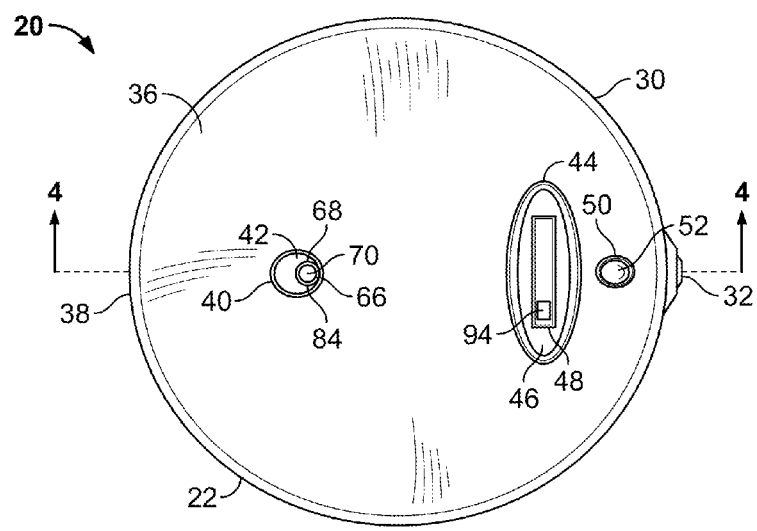
FIG. 2 is a top plan view of the actuator device of FIG. 1.
Figure 3:
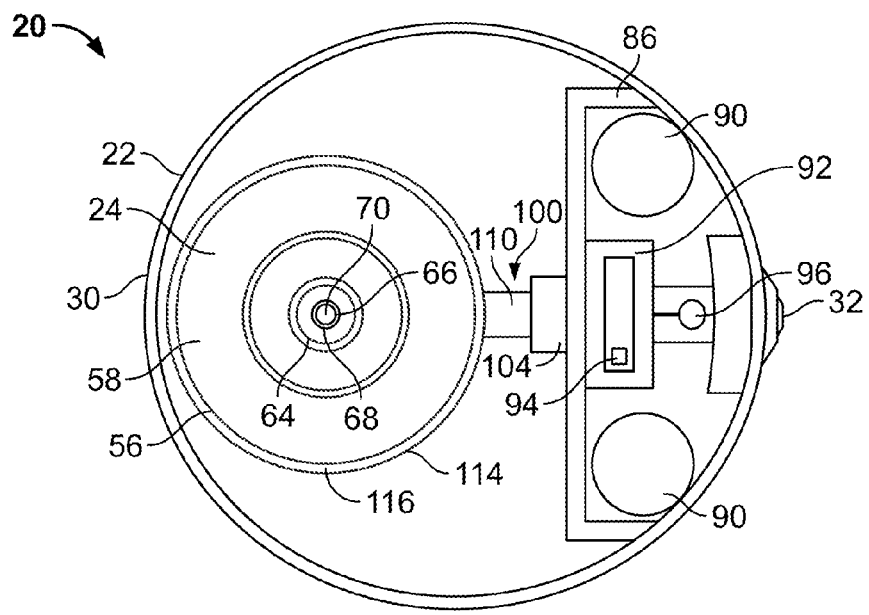
FIG. 3 is a view similar to that of FIG. 2, except that a top portion of the actuator device has been removed.

FIGS. 1-3 depict a dispenser or actuator device 20 having a generally cylindrical housing 22 adapted to retain a conventional aerosol container 24. The housing 22 includes a base portion 26 and an upper portion 28. A sidewall 30 extends between the base portion 26 and the upper portion 28 and a pushbutton 32 is disposed on the sidewall 30 proximate the base portion 26. A cylindrical rod 34 (see FIGS. 3, 4A, 4B) is provided on an interior side of the housing 22 generally opposite the pushbutton 32.

A top wall 36 of the housing 22 is convex and is bounded by a circular peripheral edge 38. A circular shaped discharge orifice 40 is disposed within the top wall 36 offset from a center thereof. An inwardly tapering wall 42 depends downwardly into an interior of the actuator device 20 about a periphery of the discharge orifice 40. A curved groove 44 is disposed between the discharge orifice 40 and the peripheral edge 38. The groove 44 includes a flat bottom 46 with a rectangular notch 48 disposed therein. An aperture 50 is also provided between the groove 44 and the peripheral edge 38. A light transmissive rod 52 is held within the aperture 50 by an interference fit. A longitudinal axis 54 of the actuator device 20 extends upwardly from the base portion 26 of the housing 22 (see FIG. 1).

In different embodiments, the housing 22 can take on other shapes, e.g. a cube, a pyramid, a cone, or any other symmetrical or nonsymmetrical shape. Further, the sidewall 30 and the top wall 36 of the housing 22 need not be continuous but can include any number of additional gaps or openings. In one example, the housing 22 comprises a frame structure that partially or fully circumscribes the container 24 and provides a support structure for various components of the actuator device 20 disclosed herein. Still further, other embodiments of the housing 22 that would be apparent to one of ordinary skill in the art may be employed without deviating from the principles described herein.

The actuator device 20 discharges fluid from the container 24 upon the occurrence of a particular condition. The condition could be the manual actuation of the actuator device 20 or the automatic actuation of the actuator device 20 in response to an electrical signal from a timer or a sensor. The fluid discharged may be a fragrance or insecticide disposed within a carrier liquid, a deodorizing liquid, or the like. The fluid may also comprise other actives, such as sanitizers, air fresheners, odor eliminators, mold or mildew inhibitors, insect repellents, and/or the like, and/or that have aromatherapeutic properties. The fluid alternatively comprises any fluid known to those skilled in the art that can be dispensed from a container. The actuator device 20 is therefore adapted to dispense any number of different fluid formulations.

The container 24 may be an aerosol container of any size and volume known to those skilled in the art. For example, the aerosol container may comprise a mini-aerosol container, such as an Oust® brand mini manufactured by S. C. Johnson and Son, Inc., of Racine, Wis. ("S. C. Johnson"), or a standard size container, such as an Oust® brand air sanitizer or a Glade® brand aerosol spray similarly manufactured by S. C. Johnson. For the purpose of describing the present embodiment, the container 24 comprises a body 56 (see FIGS. 3, 4A, and 4B) with a mounting cup 58 crimped to an upper end 60 thereof. The mounting cup 58 is generally cylindrical in shape and defines an undercut 62 proximate an upper portion of the mounting cup 58. In addition, the mounting cup 58 includes a pedestal 64 (see FIG. 3) that extends upwardly from a central portion of the mounting cup 58. A valve assembly (not shown) within the container 24 includes a valve stem 66 extending upwardly from the pedestal 64. The valve stem 66 is of the tilt-activated type similar to the one described in U.S. Pat. No. 4,068,782, which is herein incorporated by reference in its entirety. When a distal end 68 of the valve stem 66 is tilted away from the longitudinal axis 54 of the container 24 to a sufficient degree, i.e., into an operable or actuation position, the valve assembly is opened and the contents of the container 24 are discharged through a discharge orifice or end 70 in the valve stem 66. The contents of the container 24 may be discharged in a continuous or metered dose. Further, the discharging of the contents of the container 24 may be effected in any number of ways, e.g., a discharge may comprise a partial metered dose or multiple consecutive discharges.

Figure 4A:
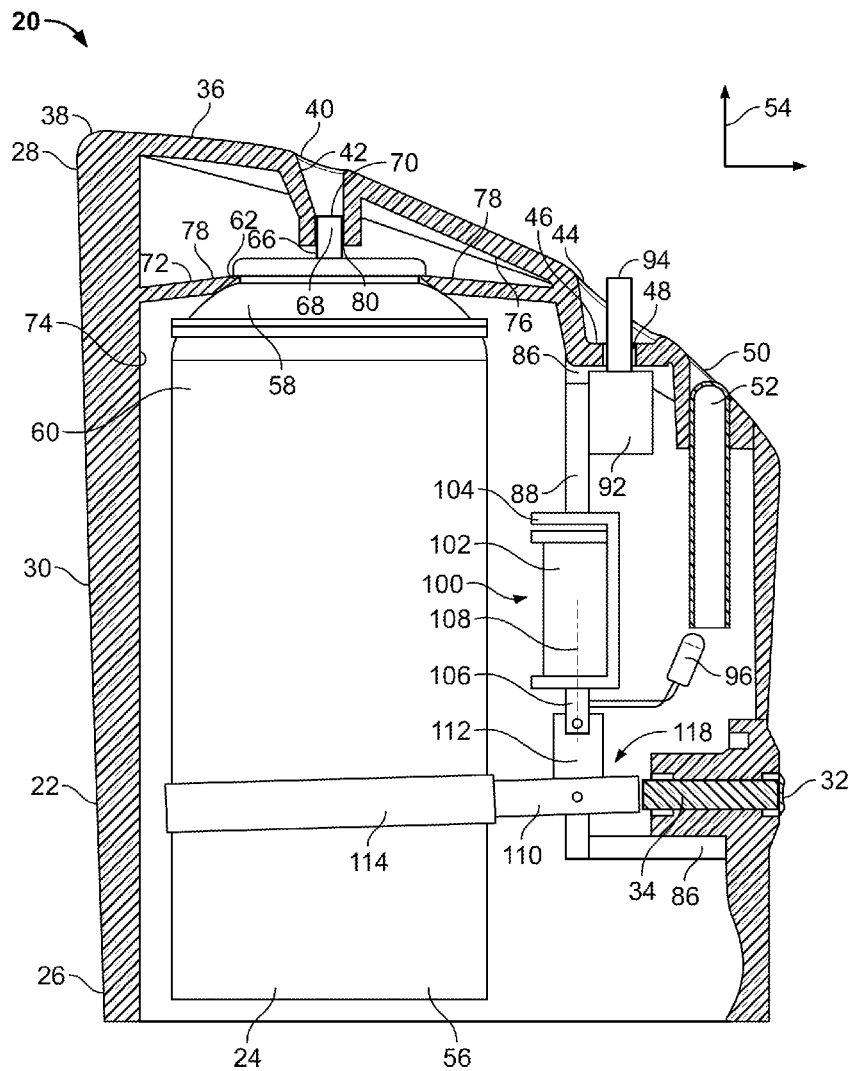
FIG. 4A is a partial cross-sectional view taken along section line 4-4 of FIG. 2 with portions of the device behind the plane of section removed for purposes of clarity to illustrate a pre-actuation position of a drive unit according to one embodiment, and wherein a container and a structure for retaining the container is also shown.
Figure 4B:
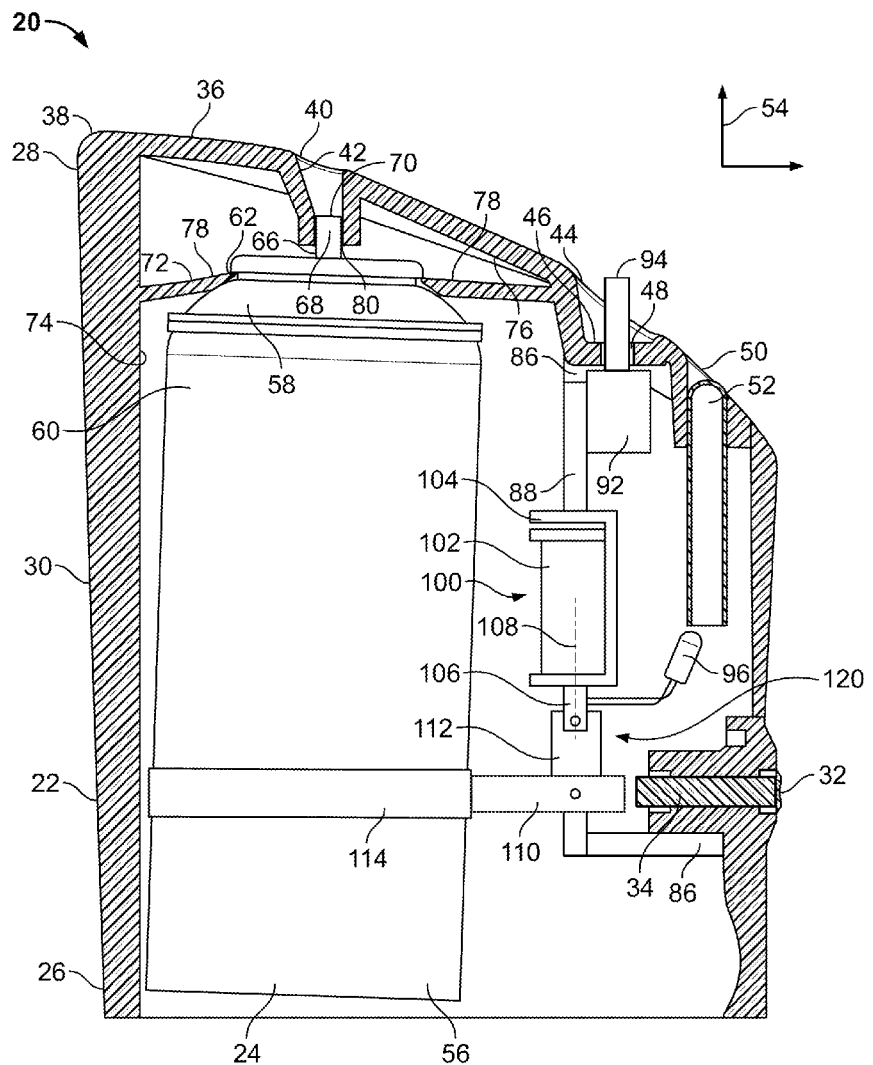
FIG. 4B is a view similar to the one shown in FIG. 4A, except that the drive unit is in a post actuation position.

With reference to FIGS. 4A and 4B, the housing 22 includes a retaining structure 72 that extends radially inwardly from an inner wall 74 of the sidewall 30 and an inner surface 76 of the top wall 36 proximate the upper portion 28 of the housing 22. More particularly, the retaining structure 72 comprises a plurality of flanges 78 molded into the housing 22 that extend radially inwardly from the sidewall 30 and the top wall 36. Distal ends of the plurality of flanges 78 are structured to resiliently bend.

The container 24 is operably placed into the housing 22 by inserting the container 24 upwardly through a bottom end of the housing 22. Continued insertion, i.e., movement of the container 24 along a path substantially parallel to the longitudinal axis 54, will cause the mounting cup 58 to interact with the retaining structure 72. Further upward movement causes the mounting cup 58 to force the resilient flanges 78 to bend over the mounting cup 58 and for the distal ends of the plurality of flanges 78 to snap into the undercut 62 of the mounting cup 58. This snap fit connection retains the container 24 in an operable position within the housing 22. The plurality of flanges 78 are sufficiently flexible to allow the container 24 to tilt with respect to the retaining structure 72 and the housing 22 as shown in FIG. 4B, but rigid enough to retain the container 24 within the housing 22. In the present embodiment, when the container 24 is retained within the housing 22 a portion of the valve stem 66 is substantially immovably seated by an interference fit within an opening 80 defined by the wall 42, which includes a generally cylindrical distal end. More particularly, when the container 24 is operably attached to the housing 22, the valve stem 66 does not substantially move with respect to the housing 22. Instead, as described in detail below, the container 24 is moved with respect to the housing 22 while the valve stem 66 is held stationary to actuate same.

Figure 5:
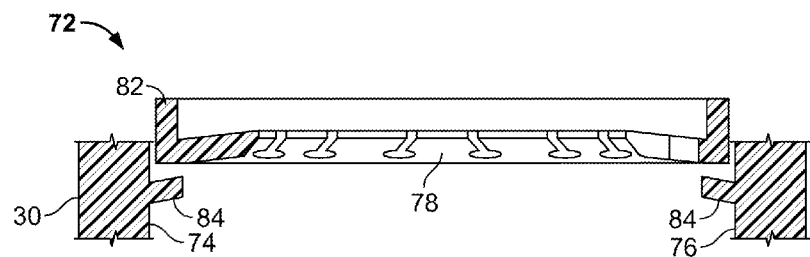
FIG. 5 is an enlarged sectional view of a second embodiment of a structure for retaining a container.
Figure 6:
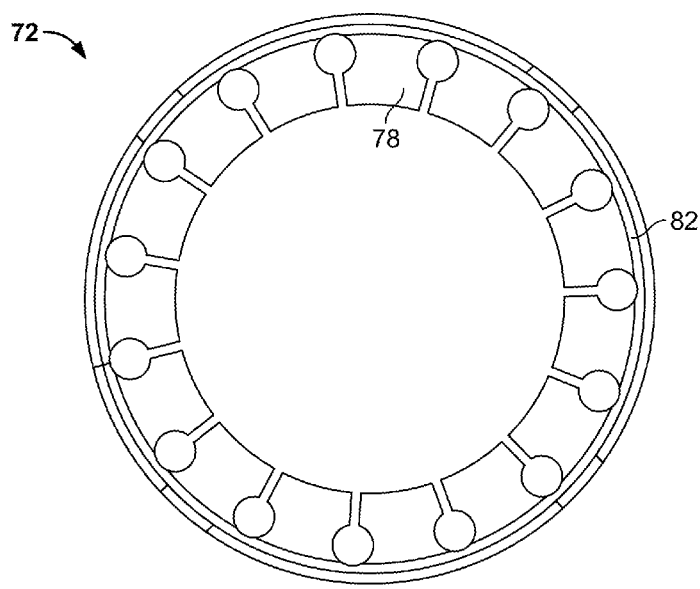
FIG. 6 is a top plan view of the structure of FIG. 5.

It is also contemplated that modifications may be made to the retaining structure 72. For example, a fewer or greater number of the plurality of flanges 78 may be provided to interact with surfaces of the container 24. The plurality of flanges 78 of the retaining structure 72 may be relatively resilient or relatively rigid depending upon the contour of the outer surface of the container 24. Further, the retaining structure 72 may be attached to the housing 22 in a fixed or removable manner or include both fixed and free portions that allow the container 24 to tilt with respect to the housing. Illustratively in FIGS. 4A and 4B, the retaining structure 72 is molded into the sidewall 30. Alternatively, FIGS. 5 and 6 depict another embodiment of the retaining structure 72, which includes the plurality of flanges 78 extending radially inwardly from an annular bracket 82. The annular bracket 82 rests freely on a platform 84 that extends from the inner wall 74 of the sidewall 30 and the inner surface 76 of the top wall 36. In another embodiment, the container 24 is attached to the retaining structure 72 via a threaded engagement (not shown). It will be apparent to one skilled in the art that numerous means exist to retain the container 24 within the housing 22. For example, in a different embodiment a retention structure similar to those shown in U.S. application Ser. No. 11/805, 976, filed on May 25, 2007, which is herein incorporated by reference in its entirety, may be provided and modified for use in connection with any of the embodiments described herein. In yet another embodiment, the retaining structure 72 is provided on the container 24 prior to insertion into the housing 22 and/or the container 24 is inserted into the housing 22 through an opening in the sidewall 30 or the top wall 36. Other embodiments utilize an interference fit between portions of the housing 22 and the container 24 to retain same within the housing 22. Further, the snap-fit and locking retaining structures described in U.S. Pat. Nos. 4,133,448, 5,027,982, and 5,649,645, which are herein incorporated by reference in their entirety, may also be adapted for use in connection with any of the embodiments described herein.

Referring to FIGS. 3, 4A, and 4B, a support 86 extends downwardly from the inner surface 76 of the top wall 36 and connects to the inner wall 74 of the sidewall 30 proximate the base portion 26 of the housing 22. The support 86 supports a printed circuit board 88 that has a control circuit (not shown) disposed thereon. The support 86 is also adapted to retain a D.C. power source 90, e.g., in the present embodiment the power source 90 comprises two AA batteries (see FIG. 3). In a different embodiment, the AA batteries are replaced by a rechargeable Nickel-Cadmium battery pack having an electrical lead (not shown) that can be used to connect the battery pack to an A.C. power outlet (not shown). In another embodiment, the D.C. power source 90 is replaced by an A.C. power adapter having an appropriate power transformer and A.C./D.C. converter as known to those skilled in the art. With reference again to FIGS. 3, 4A, and 4B, a user selectable switch assembly 92 is disposed adjacent a top portion of the printed circuit board 88. The user selectable switch assembly 92 includes a finger 94 extending upwardly therefrom and through the notch 48. The finger 94 may be used to select different operating modes for the circuit (as discussed in greater detail below). A light emitting diode (LED) 96 disposed on the printed circuit board 88 is positioned proximate the light transmissive rod 52 of the housing 22.

The control circuit allows for the electrical actuation of a drive mechanism or a drive unit 100 to cause the discharge of fluid from the container 24. As illustrated in FIGS. 4A and 4B, the drive unit 100 is a solenoid 102 disposed adjacent the circuit board 88. The drive unit 100 can be mounted to the support 86 or a portion of the circuit board 88. In the present embodiment, the solenoid 102 is a Ledex® brand C frame, Size C5, D.C. operated solenoid sold by Saia-Burgess Inc., of Vandalia, Ohio. However, other solenoids known to one of ordinary skill in the art may be employed without deviating from the principles described herein. For instance, the solenoid could be a solenoid manufactured by Tri-Tech, LLC, of Mishawaka, Ind., such as a Series 15510 Solenoid Actuator. The solenoid 102 includes a mounting brace 104 that is attached to the support 86 and/or the circuit board 88 by screws, adhesive, or any other suitable means. An armature 106 extends downwardly from the solenoid 102 toward the base portion 26 of the housing 22. In the present embodiment, a longitudinal axis 108 of the drive unit 100 is substantially parallel to the longitudinal axis 54 of the container 24. A bell crank 110 extends generally transversely to the container 24 and a connector 112 mechanically connects the armature 106 to the bell crank 110. The bell crank 110 is additionally connected to a coupling member 114 that circumscribes the body 56 of the container 24. The coupling member 114 comprises an annular portion 116 that has a diameter slightly larger than the body 56 of the container 24. When the container 24 is operably attached to the housing 22, the body 56 of the container 24 is inserted through the annular portion 116 and the mounting cup 58 of the container 24 is retained by the retaining structure 72. In this manner, the coupling member 114 secures the body 56 of the container 24 within the housing 22 and translates the downward movement of the armature 106, i.e., movement in a direction parallel to the longitudinal axis 108 of the drive unit 100, into lateral movement of the container 24, which will be described in greater detail below. In other embodiments, the coupling member 114 can be any structure or mechanism that translates movement from the drive unit 100 into lateral or transverse movement of the body 56 of the container 24.

Prior to opening the valve assembly and releasing the contents of the container 24, the armature 106, the connector 112, and the bell crank 110 are positioned in a pre-actuation position 118, such as shown in FIG. 4A. When in the pre-actuation position 118, the container 24 is held substantially parallel to the longitudinal axis 54 of the actuator device 20, i.e., a longitudinal axis of the container 24 is substantially parallel to the longitudinal axis 54. However, in other embodiments the structure internal to the housing 22 may be positioned in a different manner, insofar as a force applied to the body 56 of the container 24 can actuate the tilt valve stem 66. When the armature 106, the connector 112, and the bell crank 110 are transitioned to an actuation position 120, such as shown in FIG. 4B, the container 24 is tilted a sufficient distance away from the longitudinal axis 54 to open or actuate the valve assembly. As noted above, the valve stem 66 is retained in a substantially immovable manner. Alternatively, the container 24 may be displaced so that the valve stem 66 is in a partially open position when in the actuation position 120.

Turning to FIG. 4B, the actuation of the solenoid 102 with respect to the present embodiment will now be described with greater particularity. Upon the receipt of an actuation signal, the solenoid 102 is energized to magnetically drive the armature 106 downwardly along a path substantially parallel to the longitudinal axis 54 of the actuator device 20 and the longitudinal axis 108 of the drive unit 100. The linear motion of the armature 106 is translated into the rotational displacement of the bell crank 110 by the connector 112, which acts as a mechanical linkage therebetween. The rotational displacement of the bell crank 110 and the coupling member 114 causes the container 24 to rotate about the longitudinal axis 54 while the valve stem 66 is held in place, thereby forcing the valve stem 66 into an open position. Upon deactivation of the solenoid 102, the armature 106 is forced upwardly into the solenoid 102, thereby allowing the connector 112 and the bell crank 110 to return to the pre-actuation position 118 shown in FIG. 4A. Without any transverse forces acting to rotate the container 24 about the longitudinal axis 54, the container 24 returns to a position substantially parallel to the longitudinal axis 54 and the valve stem 66 returns to a closed position and prevents fluid discharge. The return of the container 24 to the substantially parallel position and the valve stem 66 to the closed position may be effected by one or more of a spring or spring-like mechanism (not shown), forces exerted by the mechanically linked armature 106, forces exerted by the valve assembly in the container 24, gravity, or any other means known by one skilled in the art.

The actuator device 20 of FIGS. 4A and 4B can also be manually actuated without energizing the solenoid 102. In the present embodiment, the bell crank 110 is generally aligned with the pushbutton 32 and the cylindrical rod 34. A user can press the pushbutton 32 to cause the cylindrical rod 34 to displace the bell crank 110 and manually move the container 24 to the actuation position 120 shown in FIG. 4B.

The benefits of using a tilt-activated valve stem 66 are further realized by the embodiments described herein, which tilt the container 24 while retaining the tilt-activated valve stem 66 in a substantially fixed position to actuate the valve assembly. Consequently, the forces applied to activate the valve stem 66 are further decreased by treating the container 24 as a lever arm and the retaining structure 72 as a fulcrum, wherein force is applied to a point on the container 24 distal from the retaining structure 72 via the drive unit 100 and the disclosed linkage systems.

It is anticipated that the solenoid 102 will be driven for an appropriate duration and/or appropriately displaced to fully or partially open the valve stem 66. Specific distances traveled by and/or the lengths of any of the elements, e.g., the armature 106, the connector 112, and the bell crank 110, may be modified in a manner known to those skilled in the art to adjust the mechanical relationship between the elements and to effect a partial or complete tilting of the container 24 with respect to the valve stem 66. In one embodiment, the armature 106 is held in the discharge position for a predetermined length of time or for a spraying period. The duration of the spraying period is typically equal to about 170 milliseconds. Indeed, if desired, the armature 106 could be held in the discharge position until all of the container contents are exhausted. Further, the armature 106 may be displaced multiple times in response to the occurrence of a single actuation signal to provide for multiple sequential discharges. Multiple sequential discharges may be beneficial when a single discharge from a continuously discharging container is undesirable or when intermittent discharge is desired.

Figure 7:
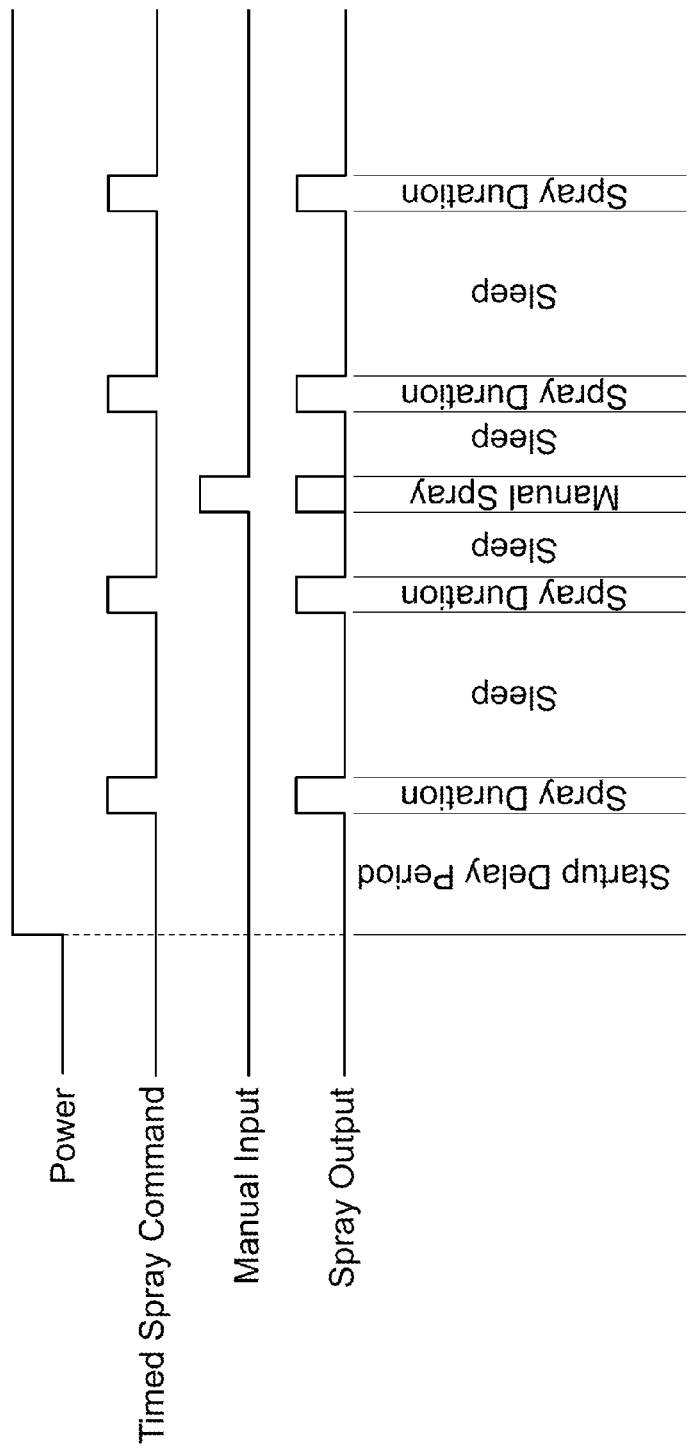
FIG. 7 is a timing diagram of the operation of the actuator device of FIGS. 1-6 according to a first operational sequence.

FIG. 7 depicts a timing diagram of the present embodiment that illustrates the operation of the actuator device 20 during an in use condition. Initially, the actuator device 20 is energized by moving the finger 94 from an "OFF" position to one of four operating modes 150, 152, 154, 156 (see FIG. 1) whereupon the actuator device 20 enters a startup delay period. Each of the four operating modes 150, 152, 154, 156 corresponds to a predetermined sleep period between consecutive spraying periods. For example, the first operating mode 150 can correspond to a five minute sleep period, the second operating mode 152 can correspond to a seven and a half minute sleep period, the third operating mode 154 can correspond to a fifteen minute sleep period, and the fourth operating mode 156 can correspond to a thirty minute sleep period. For the present example, we shall assume the first operating mode 150 has been chosen. Upon completion of the startup delay period, the solenoid 102 is directed to discharge fluid from the actuator device 20 during a first spraying period. The startup delay period is about three seconds long, and the spraying period is typically about 170 milliseconds long. Upon completion of the first spraying period, the actuator device 20 enters a first sleep period that lasts 5 minutes. Upon expiration of the first sleep period the solenoid 102 is actuated to discharge fluid during a second spraying period. Thereafter, the actuator device 20 enters a second sleep period that lasts for 5 minutes. In the present example, the second sleep period is interrupted by the manual actuation of the actuator device 20, whereupon fluid is dispensed during a third spraying period. Automatic operation thereafter continues with alternating sleep and spraying periods. At any time during a sleep period, the user can manually actuate the actuator device 20 for a selectable or fixed period of time by depressing the pushbutton 32. Upon termination of the manual spraying operation, the actuator device 20 completes the pending sleep period. Thereafter, a spraying operation is undertaken.

In another embodiment, the switch assembly 92 may be replaced and/or supplemented by a photocell motion sensor. Other motion detectors known to those of skill in the art may also be utilized, e.g., a passive infrared or gyro-electric motion sensor, an infrared reflective motion sensor, an ultrasonic motion sensor, or a radar or microwave radio motion sensor. The photocell collects ambient light and allows the control circuit to detect any changes in the intensity thereof. The control circuit undertakes filtering of the photocell output and determines if a threshold light condition has been reached, e.g., a predetermined light intensity or level of change in light intensity. If so, the control circuit develops a signal to activate the solenoid 102. For example, if the actuator device 20 is placed in a lit bathroom, a person walking past the sensor may block a sufficient amount of ambient light from reaching the sensor to cause the control circuit to activate the solenoid 102 and discharge a fluid.

It is also envisioned that the switch assembly 92 may be replaced or supplemented with a vibration sensor, an odor sensor, a heat sensor, or any other sensor known to those skilled in the art. Alternatively, more than one sensor may be provided in the actuator device 20 in lieu of the switch assembly 92 or in combination with same. It is anticipated that one skilled in the art may provide any type of sensor either alone or in combination with the switch assembly 92 and/or other sensors to meet the needs of a user. In one particular embodiment, the switch assembly 92 and a sensor are provided in the same actuator device 20. In such an embodiment, a user may choose to use the timer-based switch assembly 92 to automatically operate the drive unit 100 of the actuator device 20, or the user may choose to use the sensor to detect a given event prior to activating the actuator device 20. Alternatively, the actuator device 20 may operate in a timer and sensor based mode of operation concurrently.

In one embodiment, the LED 96 illuminates the light transmissive rod 52 when the actuator device 20 is in an operative state. The LED 96 blinks intermittently once every fifteen seconds during the sleep period. Depending on the selected operating mode, the blinking frequency of the LED 96 begins to increase as a spraying period becomes imminent. The more frequent illumination of the LED 96 serves as a visual indication that the actuator device 20 is about to discharge fluid contents into the atmosphere.

It is envisioned that different drive units 100 can be used without departing from the principles described herein. For example, the drive units described in U.S. application Ser. No. 11/801,554, filed on May 10, 2007, which is herein incorporated by reference in its entirety, may be used in connection with any of the embodiments describe herein.

Figure 8:
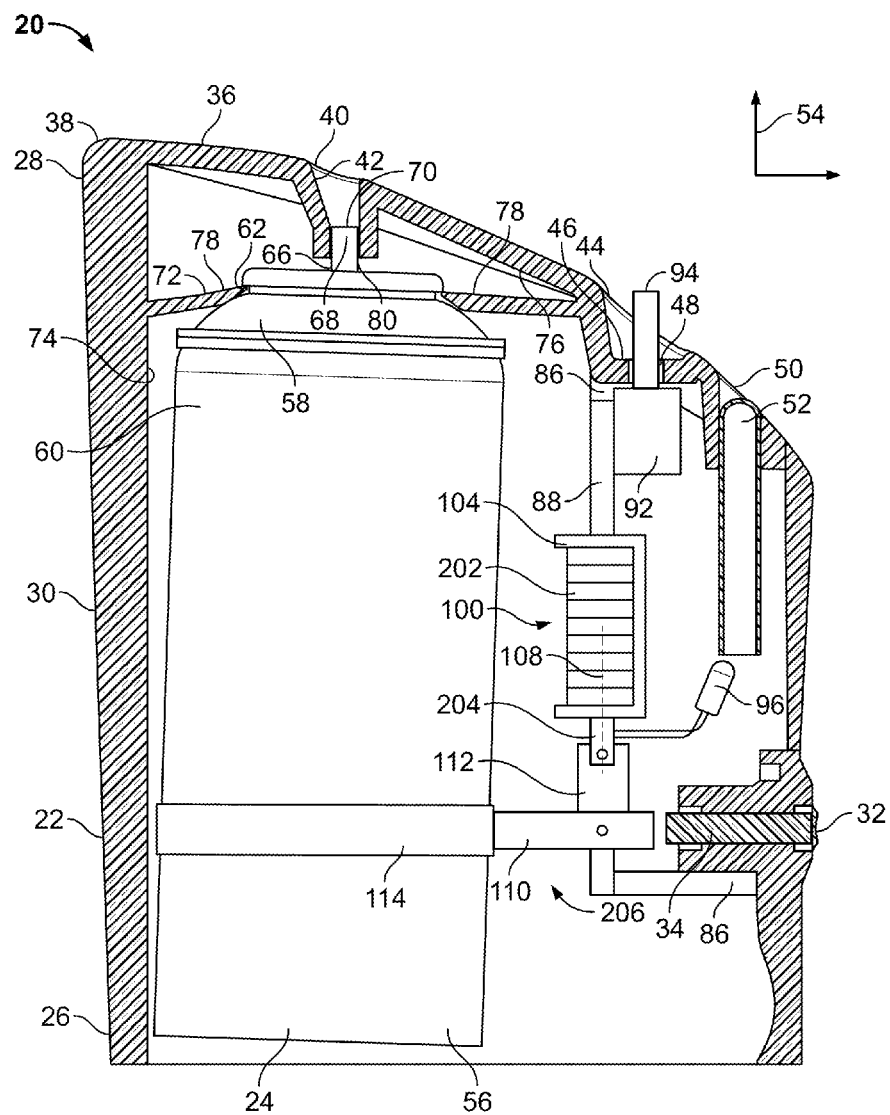
FIG. 8 is a view of a second embodiment of an actuator device similar to the view shown in FIG. 4B except that a different drive unit is provided.

In another embodiment depicted in FIG. 8, a piezo-linear motor 202 replaces the solenoid 102. The piezo-linear motor 202 includes a piezoelectric element 204, which contracts and expands linearly in a predeterminable manner when provided with a specific level of electricity. Conventional piezoelectric actuators are manufactured by stacking a plurality of piezoelectric plates or disks, wherein the stack of plates or disks expands linearly in a direction parallel to an axis of the stack. The piezo-linear motor 202 of the present embodiment may comprise a motor similar to ones manufactured by Physik Instrumente GmbH & Co., of Karlruhe, Germany. It is also anticipated that other piezoelectric devices known to those skilled in the art may be used with the embodiments disclosed herein, e.g., a piezoelectric tube actuator.

In the present embodiment, the piezoelectric element 204 transitions between a pre-actuation position (not shown) and an actuation position 206 that are substantially similar to the pre-actuation position 118 and actuation position 120, respectively, described above in connection with FIGS. 4A and 4B. In the actuation position 206 illustrated in FIG. 8, a known voltage is applied to the piezoelectric element 204, causing same to linearly expand in a direction parallel to the longitudinal axis 54 of the actuator device 20 and the longitudinal axis 108 of the drive unit 100. The displacement of the piezoelectric element 204 into the actuation position 206 causes rotational displacement of the container 24 and actuation of the valve stem 66 in a similar manner as discussed above in connection with FIG. 4B. Deenergization of the piezo-linear motor 202 allows the piezoelectric element 204 to contract and the container 24 to return to a pre-actuation position in a similar manner as discussed above in connection with FIG. 4A. The contraction and expansion sequence of the piezo-linear motor 202 may be controlled by a circuit in a similar fashion to any of the operational methodologies discussed herein or any other methodology known to one of skill in the art.

Figure 9A:
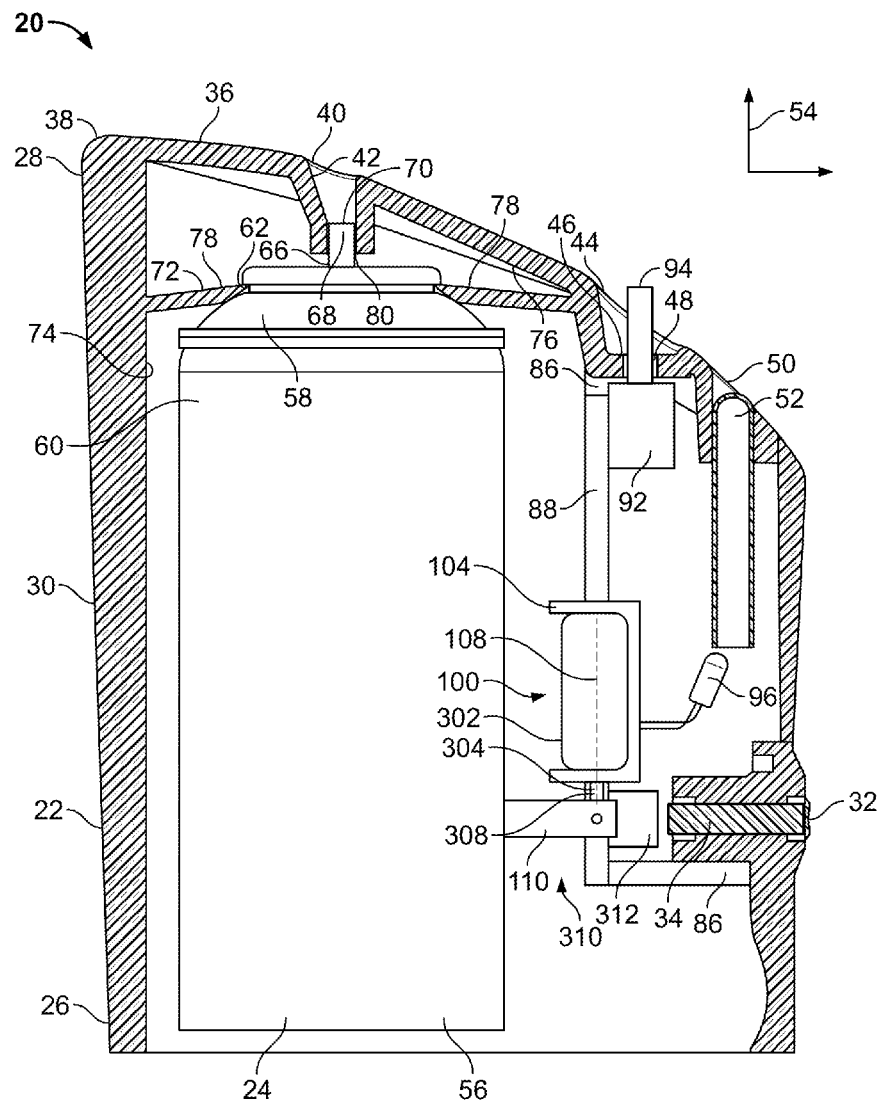
FIGS. 9A and 9B are views of a third embodiment of an actuator device similar to the view shown in FIGS. 4A and 4B, respectively, except that a different drive unit is provided.
Figure 9B:
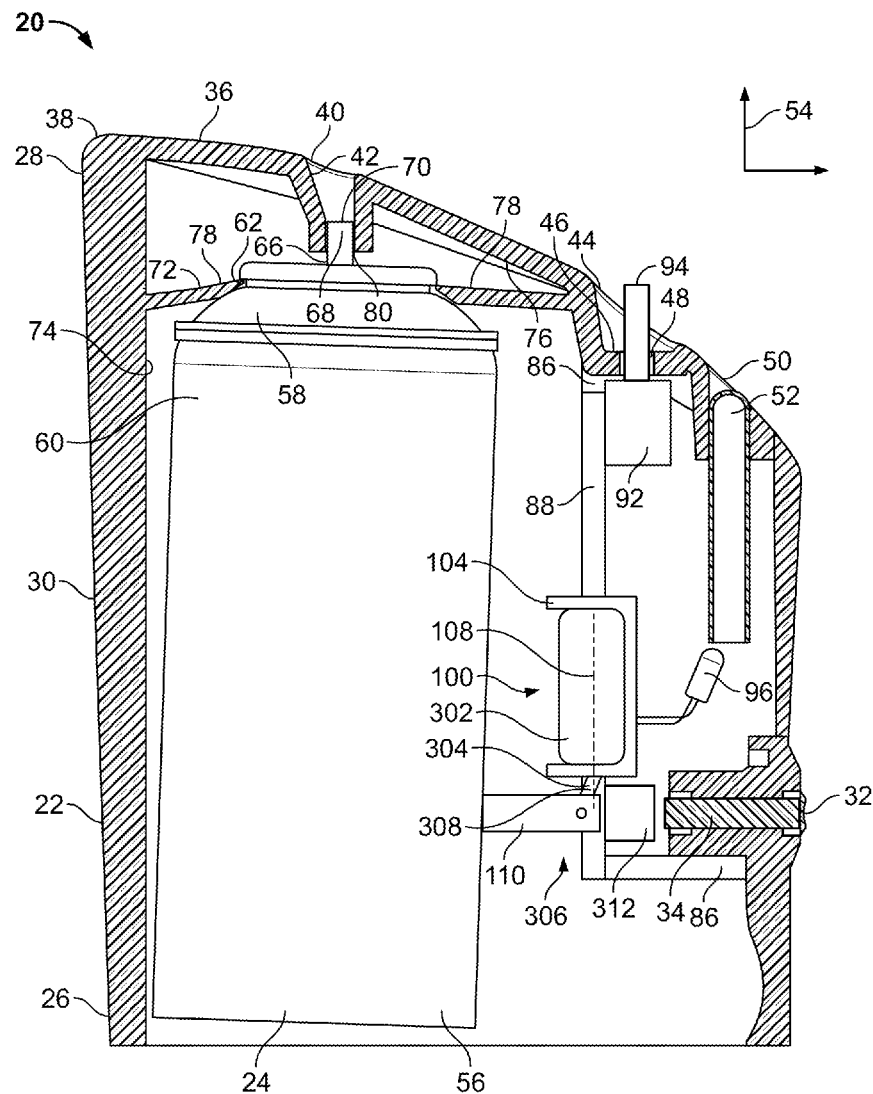

Turning now to FIGS. 9A and 9B, a different embodiment of the drive unit 100 is shown that includes a bi-metallic actuator 302 in lieu of the solenoid 102. The bi-metallic actuator 302 includes a bi-metallic element 304, which contracts and expands in a predeterminable manner when provided with heat. Conventional bi-metallic elements comprise at least two strips of metals, which exhibit different thermal expansion properties. By joining two such strips of metal together, e.g., by brazing, welding, or rivets, the bi-metallic actuator 302 will undergo a predeterminable physical transformation upon the application of a known level of heat. The bimetallic actuator 302 may include a self-contained heat source responsive to an electrical signal from a timer or a sensor. For example, the control circuitry previously described herein may be adapted to activate a heater in response to the expiration of a specified time interval. One skilled in the art will realize that many different types of heaters may be used with the embodiments described herein, e.g., an electric resistance heater, such as a metal oxide resistor, may be used with the bi-metallic actuator 302.

As illustrated in FIG. 9B, when a known level of heat is provided to the bi-metallic actuator 302, the bi-metallic element 304 transitions to an actuation position 306 and bends in a direction substantially transverse to the longitudinal axis 54 of the actuator device 20 and the longitudinal axis 108 of the drive unit 100. In the actuation position 306, a distal end 308 of the bi-metallic element 304 bends in a transverse direction toward the container 24. The bending of the bi-metallic element 304 causes rotational displacement of the container 24 and actuation of the valve stem 66 in a similar manner as discussed above in connection with FIG. 4B. When the supply of heat is terminated or a cooling operation is undertaken, the bi-metallic element 304 contracts back to a pre-actuation position 310 (see FIG. 9A) in a similar manner as discussed above in connection with FIG. 4A.

In the embodiment of FIGS. 9A and 9B, the bi-metallic element 304 is connected directly to the bell crank 110 and the bell crank 110 directly engages the container 24 instead of engaging the container 24 via a coupling member. In addition, a switch 312 is disposed on the printed circuit board 88. The switch 312 is aligned with the cylindrical rod 34 and the pushbutton 32 such that the manual depression of the pushbutton 32 causes the actuation of the switch 312. In the present embodiment, an activation signal that controls the bi-metallic actuator 302 may be generated by the control circuit automatically, e.g., during one of the operating modes 150-156 discussed above in connection with FIG. 7, in response to pressing the pushbutton 32 to activate the switch 312, or any other methodology known to one of skill in the art. Further, it is intended that the pushbutton 32 and the switch 312 arrangement be used in connection with any of the embodiments described herein to actuate the drive unit 100.

Figure 10A:
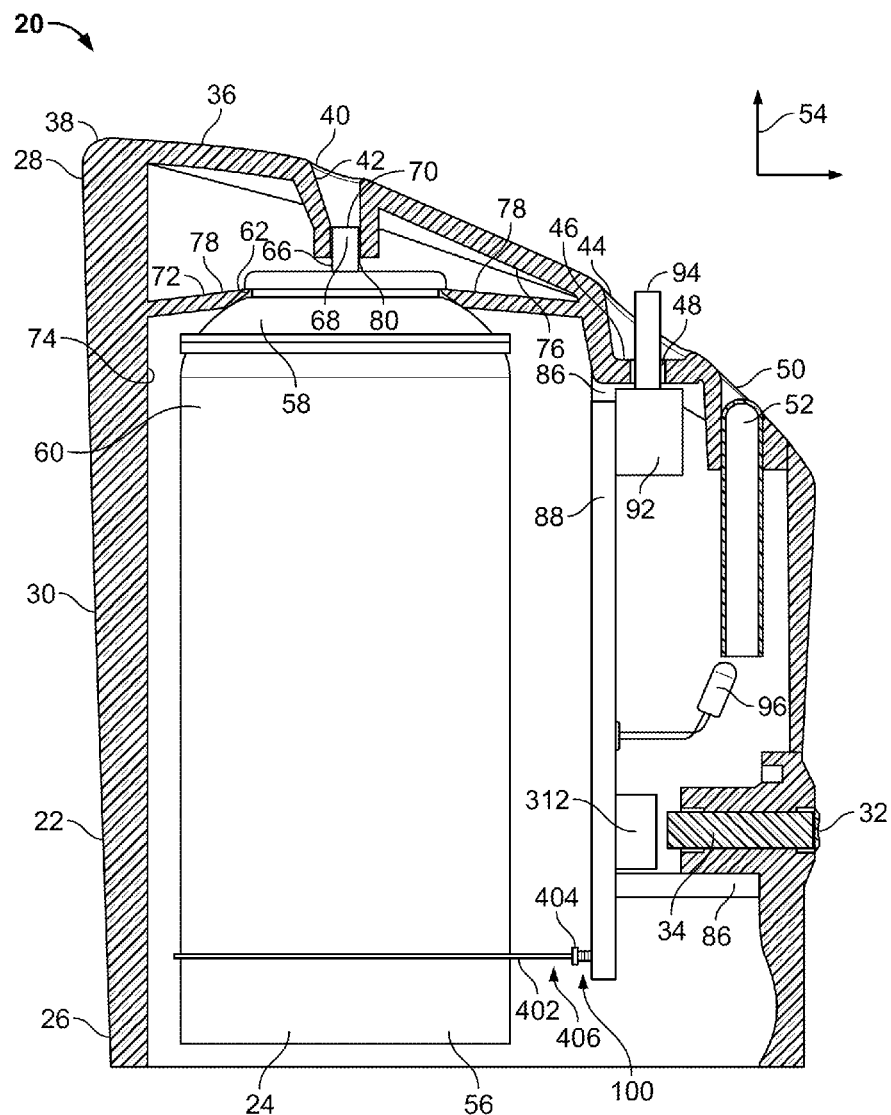
FIGS. 10A and 10B are views of a fourth embodiment of an actuator device similar to the views shown in FIGS. 4A and 4B, respectively, except that a different drive unit is shown.
Figure 10B:
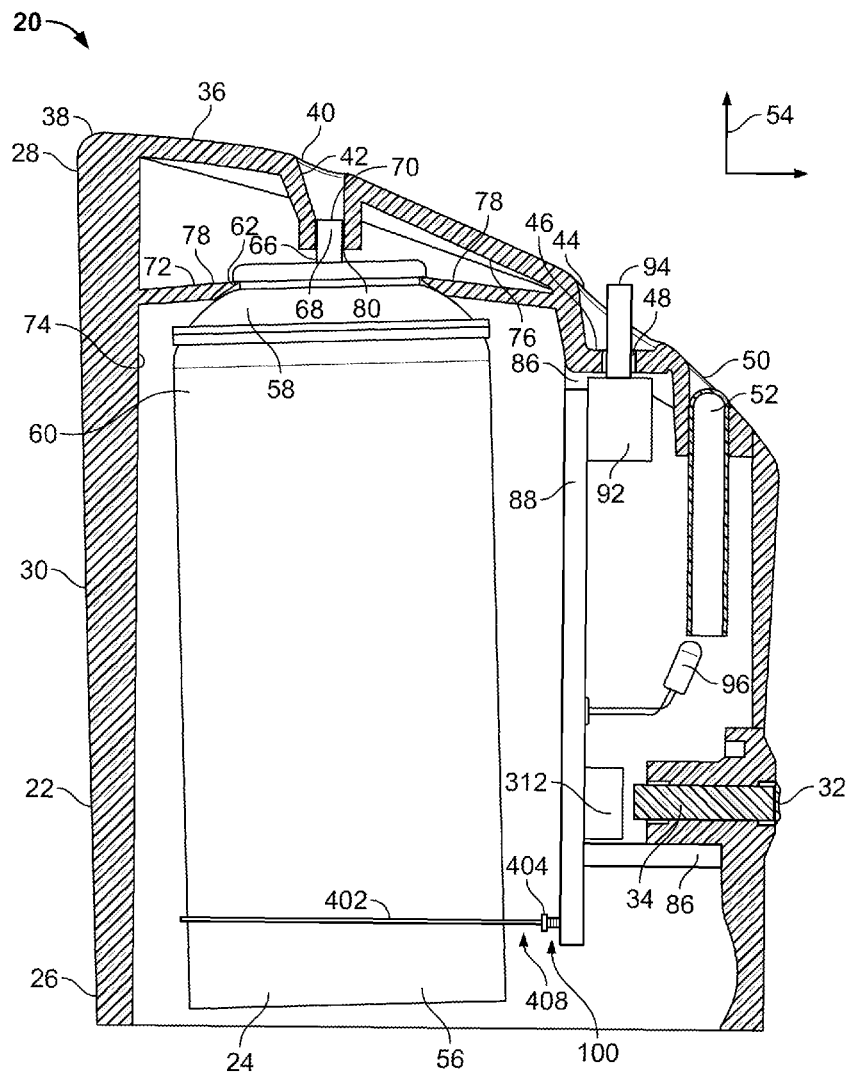

In yet another embodiment depicted in FIGS. 10A and 10B, the drive unit 100 comprises an electro-responsive wire 402, e.g., a shape memory alloy (SMA). In the present embodiment, the SMA is a nickel-titanium alloy, which is sold under the brand name Muscle Wire® by Mondo-tronics, Inc., of San Rafael, Calif. The electro-responsive wire 402 contracts and expands in a predictable manner when supplied with a known level of heat. When the electro-responsive wire 402 is connected to an electrical power source, the resistance of the wire 402 generates the heating that is required to deform the wire 402.

In the present embodiment, the electro-responsive wire 402 is wrapped around the container 24 and coupled to a wire mount 404 disposed on the support 86. In a pre-actuation position 406 shown in FIG. 10A, the electro-responsive wire 402 is spaced apart from the container 24 or is in contact with the container 24 to a degree insufficient to displace the container 24 and open the valve assembly. It is also contemplated that the actuator device 20 may be modified to facilitate the easy interface between the container 24 and the electro-responsive wire 402. Upon receipt of an activation signal, the electro-responsive wire 402 contracts and imparts a transverse motion to the container 24 sufficient to fully or partially open the valve assembly and place the container 24 in an actuation position 408 (see FIG. 10B). Deenergerzation of the electro-responsive wire 402 causes same to expand back to the pre-actuation position 406, thereby allowing the container 24 to return to a position substantially parallel to the longitudinal axis 54 and the valve stem 66 to return to a closed position (see FIG. 10A). The contraction and expansion sequence of the electro-responsive wire 402 may be controlled by a circuit in a similar fashion to any of the operational methodologies discussed herein or any other methodology known to one of skill in the art, including the use of a switch similar to the switch 312 described above in connection with FIGS. 9A and 9B.

Figure 11A:
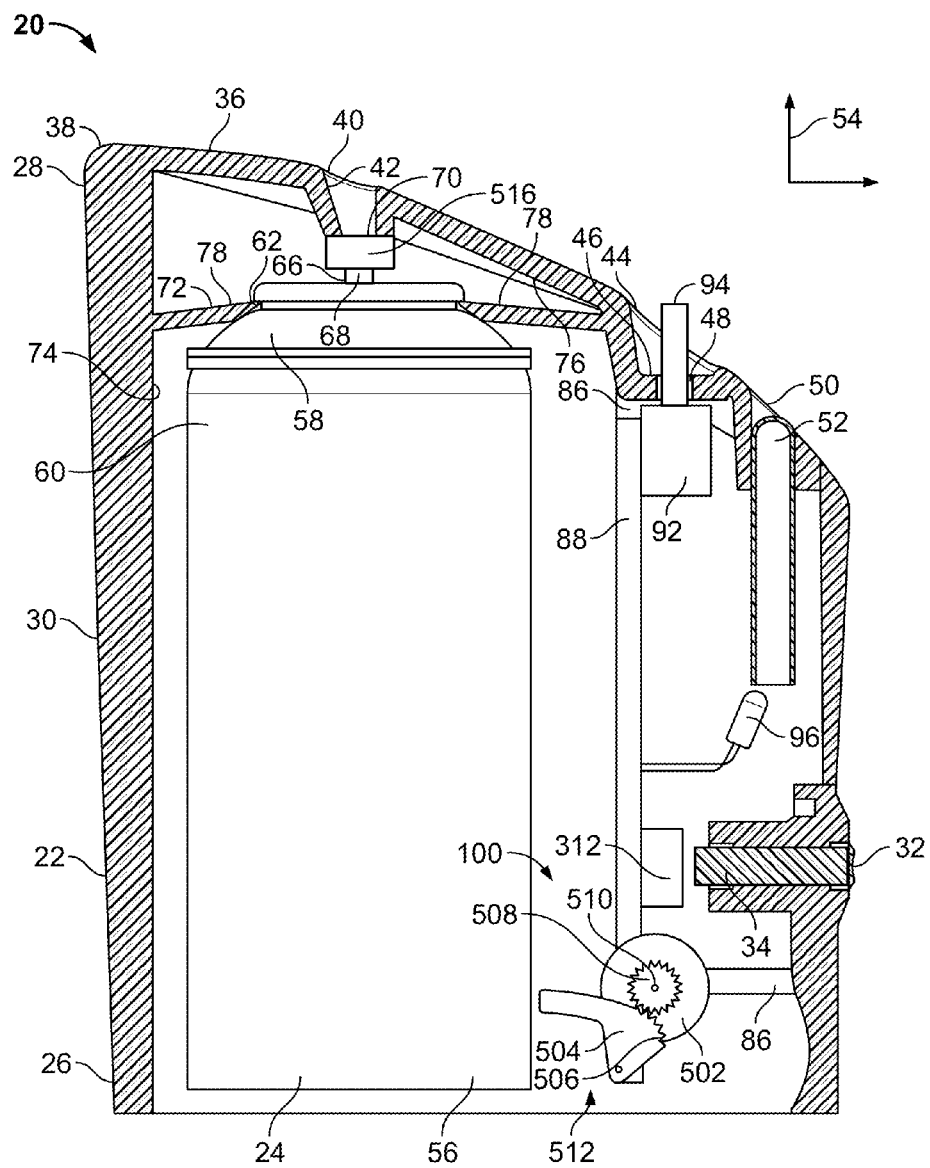
FIGS. 11A and 11B are views of a fifth embodiment of an actuator device similar to the views shown in FIGS. 4A and 4B, respectively, except that the drive unit is different.
Figure 11B:
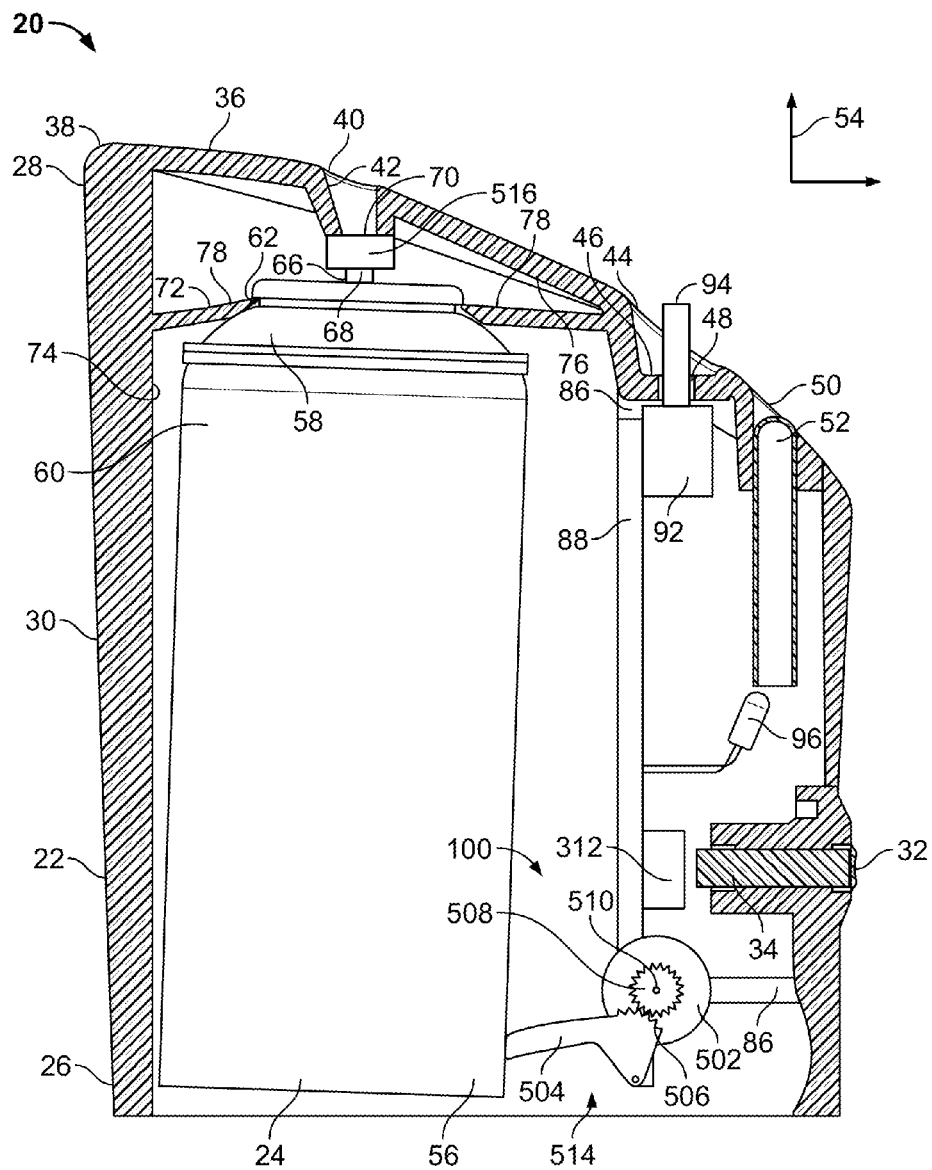

FIGS. 11A and 11B illustrate another embodiment of the drive unit 100 that includes a motor 502 and a cam member 504. The cam member 504 is integral with a reduction gear portion 506, which is operatively coupled to a pinion gear 508 disposed on a shaft 510 of the motor 502. In a pre-actuation position 512, such as shown in FIG. 11A, the cam member 504 is spaced from the container 24 or is in contact with the container 24 to a degree insufficient to displace the container 24 and open the valve assembly. Upon receipt of an activation signal, the motor 502 rotates in a counter-clockwise direction, thereby causing the cam member 504 to impart a transverse motion to the container 24 (see FIG. 11B) sufficient to move the container 24 to an actuation position 514 and fully or partially open the valve assembly. In response to a deactivation signal, the motor 502 rotates in an opposite clockwise direction to cause the cam member 504 to move back to the pre-actuation position 512, thereby allowing the container 24 to return to a position substantially parallel to the longitudinal axis 54 and the valve stem 66 to return to a closed position. The activation and deactivation of the motor 502 and cam member 504 may be controlled by a circuit in a similar fashion to any of the operational methodologies discussed herein or any other methodology known to one of skill in the art.

The present embodiment also includes a dispensing member 516 provided to secure the valve stem 66 in a position substantially parallel with the longitudinal axis 54 of the actuator device 20 and align the valve stem 66 with the discharge orifice 40. The dispensing member 516 can be secured to the valve stem 66 by an interference fit, a threaded screw engagement, a snap fit, or other types of locking means known to one of skill in the art. Further, the dispensing member 516 can be provided integrally with the housing 22 or can be otherwise secured to the housing 22. In addition, the dispensing member 516 can be similar to the one described in U.S. application Ser. No. 11/801,554, incorporated by reference above, or can be any other type of suitable dispensing member that retains and aligns the valve stem 64 with respect to the discharge orifice 40.

Figure 12:
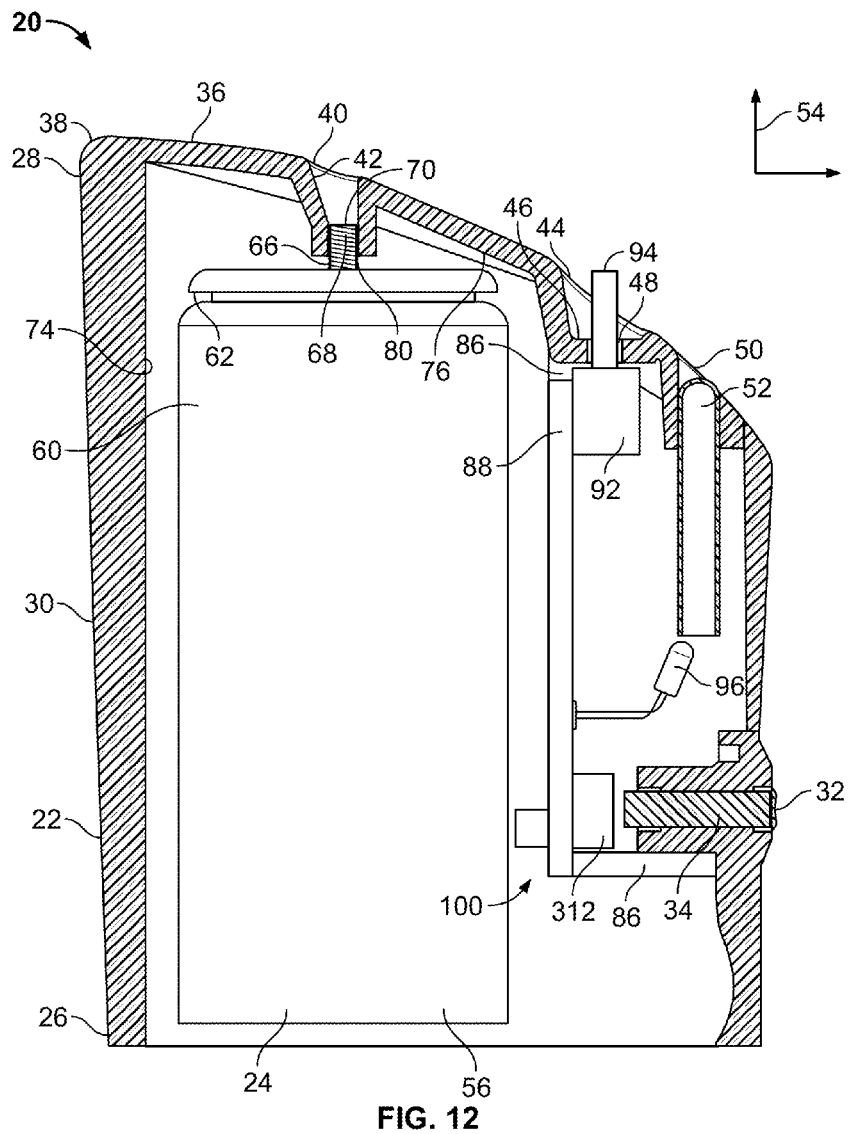
FIG. 12 is a view of a sixth embodiment of an actuator device similar to the view shown in FIG. 4A, which includes a third embodiment of a structure for retaining the container and a different drive unit.

FIG. 12 shows yet another embodiment, wherein the container 24 is retained by the housing 22 via the valve stem 66 alone. In the present embodiment, the wall 42 threadingly engages the valve stem 66 to secure same thereto. In a different embodiment, the valve stem 66 is secured to the wall 42 by an interference fit, a snap-fit, or any other means known to one of ordinary skill in the art. Further, any of the drive units 100 disclosed herein can be used in the present embodiment to displace the container 24 and actuate the valve stem 66.

Figure 13:
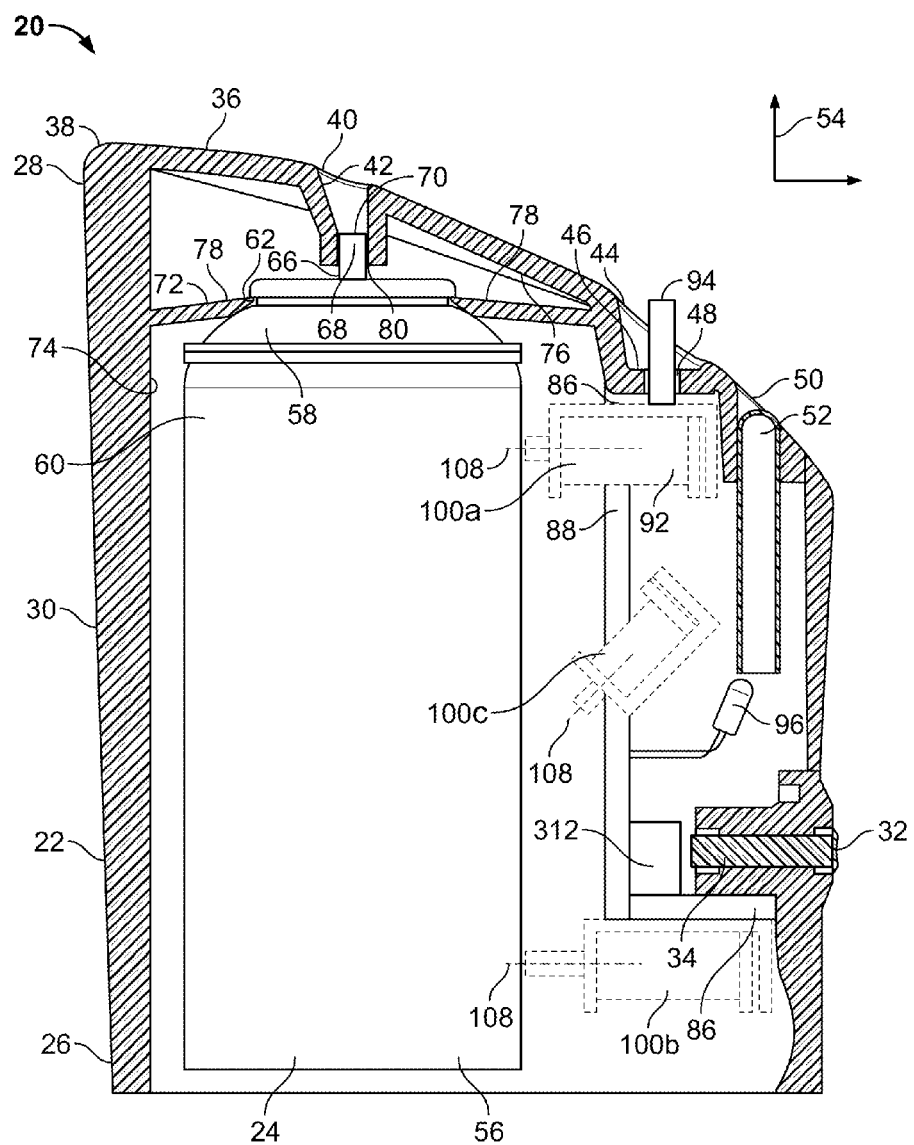
FIG. 13 is a view similar to the view shown in FIG. 4A, wherein various positions and orientations of a drive unit are depicted.

It is also envisioned that the drive unit 100 can be disposed in different operable positions and/or orientations without departing from the principles described herein. Likewise, it is envisioned that other mechanical linkage systems may be used to impart rotational movement and transverse forces to the container 24. Illustratively in FIG. 13, drive units 100*a*, 100*b*, and 100*c* are positioned proximate a top of the container 24, a bottom of the container 24, and therebetween, respectively. It is envisioned that the drive units 100*a-c* may be positioned anywhere about the body 56 of the container 24. Further, the drive unit 100 may be positioned in any number of orientations, wherein the central axis 108 of the drive unit 100 is parallel to, perpendicular to, or at any other angle relative to the longitudinal axis 54 of the actuator device 20 (see drive unit 100*c*). It will be apparent to those skilled in the art how the bell crank 108 and/or the connector 110 can be adjusted to remain in operable communication with the container 24 and the drive unit 100. In other embodiments, the connector 110 can be omitted or additional connectors or arms may be included to form an operable mechanical linkage system. Still further, U.S. application Ser. No. 11/801,554, incorporated by reference above, discloses other orientations of drive units and mechanical linkage systems that can be used in connection with any of the embodiments described herein.

Any of the embodiments described herein may be modified to include any of the structures or methodologies disclosed in connection with different embodiments. It is also contemplated that any of the drive units 100 may be modified or provided with additional structure to enhance their function and/or operability, e.g., to increase the force applied to the container 24 from the drive unit 100. The present embodiments may also be modified to enhance consumer interaction with the actuator device or assist in inserting and/or aligning a container within the actuator device. Further, the present disclosure is not limited to containers of the type specifically shown. Indeed, the actuator devices of any of the embodiments disclosed herein may be modified to work with any type of aerosol or non-aerosol tilt-activated container. However, it is also contemplated that structure may be provided to prevent certain containers from being utilized to prevent damage to the container and/or the actuator device.

INDUSTRIAL APPLICABILITY

The actuator device described herein advantageously combines an aerosol container including a tilt-activated valve stem and a drive unit that engages the aerosol container to place the valve stem in an operable position. Further, a control circuit is provided to allow the actuator device to automatically place the valve stem in the operable position and dispense the contents of the container. The placement of the valve stem in the operable position can be in response to a number of different sources, e.g., a selectable switch, a manual pushbutton, and/or various sensors.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

We claim:

1. A volatile material dispenser, comprising:
   a container;
   a housing adapted to receive the container having a tilt-activated valve stem, wherein the housing includes a resilient retaining structure, and wherein the resilient retaining structure is a fulcrum, which is adapted to retain a portion of the container and to bend to allow the container to tilt from a pre-actuated position to an actuated position and is adapted to dispense a volatile material in an upward direction; and
   an electric drive unit disposed within the housing, wherein the drive unit includes a cam for engaging a portion of the container to actuate the valve stem.

2. The volatile material dispenser of claim 1, wherein the cam engages a lower portion of the container.

3. The volatile material dispenser of claim 1, wherein the resilient retaining structure retains the container by an upper portion thereof.

4. The volatile material dispenser of claim 3, wherein the resilient retaining structure is adapted to retain the container in an operable position by interaction with a body of the container.

5. The volatile material dispenser of claim 3, wherein the upper portion of the container retained by the resilient retaining structure does not include the valve stem of the container.

6. The volatile material dispenser of claim 1, wherein a discharge end of the valve stem is adapted to be in fluid communication with a discharge orifice of the housing.

7. The volatile material dispenser of claim 1, wherein the container is wholly contained within the housing.

8. The volatile material dispenser of claim 1, wherein an electronic signal to activate the electric drive unit is generated by at least one of a sensor, a timing circuit, and the actuation of a manual pushbutton.

9. The volatile material dispenser of claim 1 further including the container.

10. A volatile material dispenser, comprising:
    a housing adapted to retain a container in a substantially upright, suspended operable position, wherein the container includes a tilt-activated valve stem; and
    a drive unit disposed within the housing, wherein the drive unit includes a cam having a gear portion, which imparts transverse motion to a body of the container.

11. The volatile material dispenser of claim 10, wherein the cam imparts transverse motion by engaging a lower portion of the body of the container.

12. The volatile material dispenser of claim 10, wherein the container is retained by an upper portion thereof.

13. The volatile material dispenser of claim 12, wherein the container is retained by interaction with the body of the container.

14. The volatile material dispenser of claim 12, wherein the upper portion of the container retained by the housing does not include the valve stem of the container.

15. The volatile material dispenser of claim 10, wherein a discharge end of the valve stem is adapted to be in fluid communication with a discharge orifice of the housing.

16. The volatile material dispenser of claim 10, wherein the container is wholly contained within the housing.

17. The volatile material dispenser of claim 10, wherein an electronic signal to activate the drive unit is generated by at least one of a sensor, a timing circuit, and the actuation of a manual pushbutton.

* * * * *